(12) United States Patent
Chalekian (10) Patent No.: US 10,105,220 B2
(45) Date of Patent: Oct. 23, 2018

(54) TRANSAPICAL PASSIVE ARTICULATION DELIVERY SYSTEM DESIGN

(71) Applicant: St. Jude Medical, Cardiology Division, Inc., St. Paul, MN (US)

(72) Inventor: Aaron J. Chalekian, Savage, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 388 days.

(21) Appl. No.: 14/769,000

(22) PCT Filed: Dec. 30, 2013

(86) PCT No.: PCT/US2013/078306
§ 371 (c)(1),
(2) Date: Aug. 19, 2015

(87) PCT Pub. No.: WO2014/130160
PCT Pub. Date: Aug. 28, 2014

(65) Prior Publication Data
US 2016/0000561 A1    Jan. 7, 2016

Related U.S. Application Data

(60) Provisional application No. 61/767,424, filed on Feb. 21, 2013.

(51) Int. Cl.
*A61F 2/24* (2006.01)

(52) U.S. Cl.
CPC .......... *A61F 2/2427* (2013.01); *A61F 2/2436* (2013.01)

(58) Field of Classification Search
CPC .. A61F 2002/011; A61F 2/2427; A61F 2/243; A61F 2/2433; A61F 2/2436;
(Continued)

(56) References Cited

U.S. PATENT DOCUMENTS

| 3,384,088 A | 5/1968 | Miseo |
| 3,657,744 A | 4/1972 | Ersek |

(Continued)

FOREIGN PATENT DOCUMENTS

| EP | 1129744 A1 | 9/2001 |
| EP | 1157673 A2 | 11/2001 |

(Continued)

OTHER PUBLICATIONS

International Search Report for Application No. PCT/US2013/078306 dated May 2, 2014.

(Continued)

*Primary Examiner* — Jonathan Miles
(74) *Attorney, Agent, or Firm* — Lerner, David, Littenberg, Krumholz & Mentlik, LLP (57) ABSTRACT

A delivery system (100) for delivering a collapsible prosthetic heart valve includes a body (120) extending in a longitudinal direction and a sheath (130) slidable relative to the body. A compartment (155) is defined inside the sheath and is adapted to receive the collapsible prosthetic heart valve in a collapsed condition. The system includes an articulating joint having a first portion operatively connected to the compartment and a second portion operatively connected to the body. The first portion is pivotable relative to the second position so as to pivot the sheath from a first orientation extending in the longitudinal direction to a second orientation extending transverse to the longitudinal direction.

17 Claims, 7 Drawing Sheets (58) Field of Classification Search
CPC .......... A61F 2/2439; A61F 2/95; A61F 2/954;
A61F 2/958; A61F 2002/9583; A61F
2002/9586; A61F 2/962; A61F 2/966;
A61F 2002/9665; A61F 2/97
See application file for complete search history.

(56) References Cited

U.S. PATENT DOCUMENTS

| | | | |
|---|---|---|---|
| 3,724,238 | A | 4/1973 | Retali et al. |
| 4,423,730 | A | 1/1984 | Gabbay |
| 4,641,657 | A | 2/1987 | Ellis |
| 5,368,592 | A | 11/1994 | Stern et al. |
| 5,372,587 | A | 12/1994 | Hammerslag et al. |
| 5,405,344 | A | 4/1995 | Williamson et al. |
| 5,507,725 | A | 4/1996 | Savage et al. |
| 5,549,594 | A | 8/1996 | Brunken |
| 5,569,270 | A | 10/1996 | Weng |
| 5,575,799 | A | 11/1996 | Bolanos et al. |
| 5,749,881 | A | 5/1998 | Sackier et al. |
| 5,843,167 | A | 12/1998 | Dwyer et al. |
| 5,868,685 | A | 2/1999 | Powell et al. |
| 5,924,424 | A | 7/1999 | Stevens et al. |
| 5,968,068 | A | 10/1999 | Dehdashtian et al. |
| 6,077,297 | A | 6/2000 | Robinson et al. |
| 6,183,432 | B1 | 2/2001 | Milo |
| 6,306,141 | B1 | 10/2001 | Jervis |
| 6,623,518 | B2 | 9/2003 | Thompson et al. |
| 6,743,239 | B1 | 6/2004 | Kuehn et al. |
| 6,814,746 | B2 | 11/2004 | Thompson et al. |
| 6,830,584 | B1 | 12/2004 | Seguin |
| 7,018,406 | B2 | 3/2006 | Seguin et al. |
| 7,300,431 | B2 | 11/2007 | Dubrovsky |
| 7,311,730 | B2 | 12/2007 | Gabbay |
| 7,344,553 | B2 * | 3/2008 | Opolski .............. A61B 17/0057 606/205 |
| 7,510,572 | B2 | 3/2009 | Gabbay |
| 7,637,905 | B2 | 12/2009 | Saadat et al. |
| 7,682,390 | B2 | 3/2010 | Seguin |
| 7,803,185 | B2 | 9/2010 | Gabbay |
| 7,811,277 | B2 | 10/2010 | Boulais |
| 9,227,990 | B2 | 1/2016 | Phull et al. |
| 2001/0020173 | A1 * | 9/2001 | Klumb .................... A61F 2/88 606/194 |
| 2003/0050694 | A1 | 3/2003 | Yang et al. |
| 2003/0233108 | A1 | 12/2003 | Gellman et al. |
| 2004/0210304 | A1 | 10/2004 | Seguin et al. |
| 2005/0137622 | A1 | 6/2005 | Griffin |
| 2005/0137695 | A1 | 6/2005 | Salahieh et al. |
| 2005/0137697 | A1 | 6/2005 | Salahieh et al. |
| 2005/0165352 | A1 | 7/2005 | Henry et al. |
| 2005/0177138 | A1 | 8/2005 | Dubrovsky |
| 2006/0058872 | A1 | 3/2006 | Salahieh et al. |
| 2006/0074484 | A1 | 4/2006 | Huber |
| 2006/0106415 | A1 | 5/2006 | Gabbay |
| 2006/0142848 | A1 | 6/2006 | Gabbay |
| 2006/0167468 | A1 | 7/2006 | Gabbay |
| 2006/0235502 | A1 | 10/2006 | Belluche et al. |
| 2006/0259120 | A1 | 11/2006 | Vongphakdy et al. |
| 2007/0010876 | A1 | 1/2007 | Salahieh et al. |
| 2007/0027534 | A1 | 2/2007 | Bergheim et al. |
| 2007/0043259 | A1 | 2/2007 | Jaffe et al. |
| 2007/0043435 | A1 | 2/2007 | Seguin et al. |
| 2007/0055358 | A1 | 3/2007 | Krolik et al. |
| 2007/0073376 | A1 | 3/2007 | Krolik et al. |
| 2007/0073391 | A1 | 3/2007 | Bourang et al. |
| 2007/0088431 | A1 | 4/2007 | Bourang et al. |
| 2007/0112422 | A1 | 5/2007 | Dehdashtian |
| 2007/0162100 | A1 | 7/2007 | Gabbay |
| 2007/0168013 | A1 * | 7/2007 | Douglas .................... A61F 2/07 623/1.12 |
| 2007/0203575 | A1 | 8/2007 | Forster et al. |
| 2007/0239271 | A1 | 10/2007 | Nguyen |
| 2007/0244552 | A1 | 10/2007 | Salahieh et al. |
| 2008/0065122 | A1 | 3/2008 | Stack et al. |
| 2008/0071369 | A1 | 3/2008 | Tuval et al. |
| 2008/0147182 | A1 | 6/2008 | Righini et al. |
| 2008/0228223 | A1 | 9/2008 | Alkhatib |
| 2009/0054975 | A1 | 2/2009 | del Nido et al. |
| 2009/0062606 | A1 | 3/2009 | Ueda et al. |
| 2009/0062839 | A1 | 3/2009 | Kurrus |
| 2010/0004740 | A1 | 1/2010 | Seguin et al. |
| 2010/0286768 | A1 | 11/2010 | Alkhatib |
| 2010/0298931 | A1 | 11/2010 | Quadri et al. |
| 2011/0098800 | A1 | 4/2011 | Braido et al. |
| 2011/0207999 | A1 | 8/2011 | Torisawa et al. |
| 2011/0224678 | A1 | 9/2011 | Gabbay |
| 2012/0078350 | A1 | 3/2012 | Wang et al. |
| 2013/0297012 | A1 | 11/2013 | Willard |
| 2013/0297102 | A1 | 11/2013 | Hughes et al. |

FOREIGN PATENT DOCUMENTS

| | | |
|---|---|---|
| EP | 1716822 A1 | 11/2006 |
| EP | 1926455 | 6/2008 |
| FR | 2765098 A1 | 12/1998 |
| WO | 2006138173 A2 | 12/2006 |
| WO | 07071436 A2 | 6/2007 |
| WO | 08070797 A2 | 6/2008 |
| WO | 10051025 A1 | 5/2010 |
| WO | 10087975 A1 | 8/2010 |
| WO | 2010127162 A1 | 11/2010 |

OTHER PUBLICATIONS

International Search Report and Written Opinion for Application No. PCT/US2013/039405 dated Sep. 23, 2013.

Quaden, Rene, et al., Percutaneous aortic valve replacement: resection before implantation, 836-840, European J. of Cardio-thoracic Surgery, 27 (2005).

Ruiz, Carlos, Overview of PRE-CE Mark Transcatheter Aortic Valve Technologies, Euro PCR, May 25, 2010.

* cited by examiner

TRANSAPICAL PASSIVE ARTICULATION DELIVERY SYSTEM DESIGN

CROSS-REFERENCE TO RELATED APPLICATION

This application is a national phase entry under 35 U.S.C. § 371 of International Application No. PCT/US2013/078306, filed Dec. 30, 2013, which claims priority to U.S. Provisional Patent Application No. 61/767,424, filed on Feb. 21, 2013, the disclosures of which are incorporated herein by reference.

BACKGROUND OF THE INVENTION

The present invention is related to prosthetic heart valve replacement, and more particularly to devices, systems, and methods for transcatheter delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparascopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valves structures are ordinarily mounted: a self-expanding stent and a balloon-expandable stent. To place such valves into a delivery apparatus and ultimately into a patient, the valve must first be collapsed or crimped to reduce its circumferential size. These collapsible and re-expandable prosthetic heart valves can then be implanted transapically or percutaneously through the arterial system, such as through the femoral artery.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically begins to expand as the sheath covering the valve is withdrawn.

In conventional delivery systems for self-expanding aortic valves, for example, after the delivery system has been positioned for deployment, the annulus end of the valve is typically unsheathed and expanded first, while the aortic end of the valve remains sheathed. Once the annulus end of the valve has expanded, it may be determined that the valve needs to be repositioned in the patient's aortic annulus. To accomplish this, a user (such as a surgeon or an interventional cardiologist) typically resheathes the annulus end of the valve, so that the valve can be repositioned while in a collapsed state. After the valve has been repositioned, the user can again release the valve.

As stated above, collapsible prosthetic heart valves may be delivered to the valve annulus, and particularly the aortic valve annulus, either transfemorally or transapically, as well as by other percutaneous procedures. In transfemoral valve implantation, the collapsible prosthetic heart valve is introduced through the femoral artery and is ultimately delivered in a retrograde manner through the aortic arch to the native aortic valve annulus. In transapical valve implantation, the collapsible prosthetic heart valve is delivered in an antegrade fashion through the apex of the heart to the native aortic valve annulus.

In transapical valve implantation, it would be preferable if the axis of the entry point at the apex of the heart was coaxial with the axis of the annulus of the aortic heart valve. This would allow a straight transapical valve delivery device to enter the left ventricle through the apex of the heart and move in a straight line directly through the center of the annulus area of the aortic heart valve. However, in patients with diseased hearts and heart valves, there can be a mismatch of up to 30 or 40 degrees between the apical and annular axes. Moreover, tissue structures within the heart may interfere with a straight path from the apex of the heart to the center of the aortic valve annulus. These structural issues can add additional difficulty to the process of correctly aligning a prosthetic heart valve at the site of implantation.

Despite the various improvements that have been made to the collapsible prosthetic heart valve delivery process, conventional delivery devices, systems, and methods suffer from some shortcomings. For example, prosthetic valve delivery devices have not yet fully addressed patient specific mismatches between the apical and annular axes or the heart or the presence of interfering tissue structures.

There therefore is a need for further improvements to the devices, systems, and methods for transcatheter delivery of collapsible prosthetic heart valves, and in particular, self-expanding prosthetic heart valves. Among other advantages, the present invention may address one or more of these needs.

BRIEF SUMMARY OF THE INVENTION

The present disclosure relates to delivery systems for delivering a medical device to an implantation site in a patient, such as a collapsible prosthetic heart valve. In one embodiment, a delivery system includes a body extending in a longitudinal direction. A sheath is slidable relative to the body, and a compartment is defined inside the sheath and is adapted to receive the medical device in an assembled condition. The system also includes an articulating joint having a first portion operatively connected to the sheath and a second portion operatively connected to the body. The first portion is pivotable relative to the second portion so as to pivot the sheath from a first orientation extending in the longitudinal direction to a second orientation extending transverse to the longitudinal direction. The articulating joint can include a ball and a socket. The system can further include a restrictive sheath slidable relative to the articulating joint between a lock position and a release position. The restrictive sheath, when in the lock position, at least partially circumscribes the articulating joint. When in the release position, the restrictive sheath at most partially circumscribes the articulating joint. The restrictive sheath can include a slot having with a width less than the width of the first portion of the articulating joint. The first portion of the articulating joint may be configured to pivot through the slot in a single plane when the restrictive sheath is in the release position. The restrictive sheath may include proximal and distal portions, and the distal portion may be proximal to the first portion of the articulating joint when the restrictive sheath is in the release position. In this release position, the first portion of the articulating joint may be configured to pivot in any plane relative to the second portion of the articulating joint.

The restrictive sheath of the delivery system may also be rotatable about an axis extending in the longitudinal direction. The restrictive sheath may also be operably connected to a retraction mechanism at a proximal end of the delivery system. The retraction mechanism can be a wheel. The restrictive sheath may also include visual indicia of location, such as line markings or fluoroscopic markings. The delivery system may further include a locking feature configured to compress the socket toward the ball. The locking feature can be a locking sheath slidable between a lock condition surrounding a largest cross-section of the socket and a release condition not surrounding the largest cross-section of the socket. The locking feature can alternately be a chuck.

BRIEF DESCRIPTION OF THE DRAWINGS

Various embodiments of the present invention will now be discussed with reference to the appended drawings. It is to be appreciated that these drawings depict only some embodiments of the invention and are therefore not to be considered limiting of its scope.

DETAILED DESCRIPTION

As used herein, the terms "proximal" and "distal" are to be taken as relative to a user (e.g., a surgeon or an interventional cardiologist) of the disclosed delivery devices. "Proximal" is to be understood as relatively close to the user and "distal" is to be understood as relatively farther away from the user.

Figure 1:
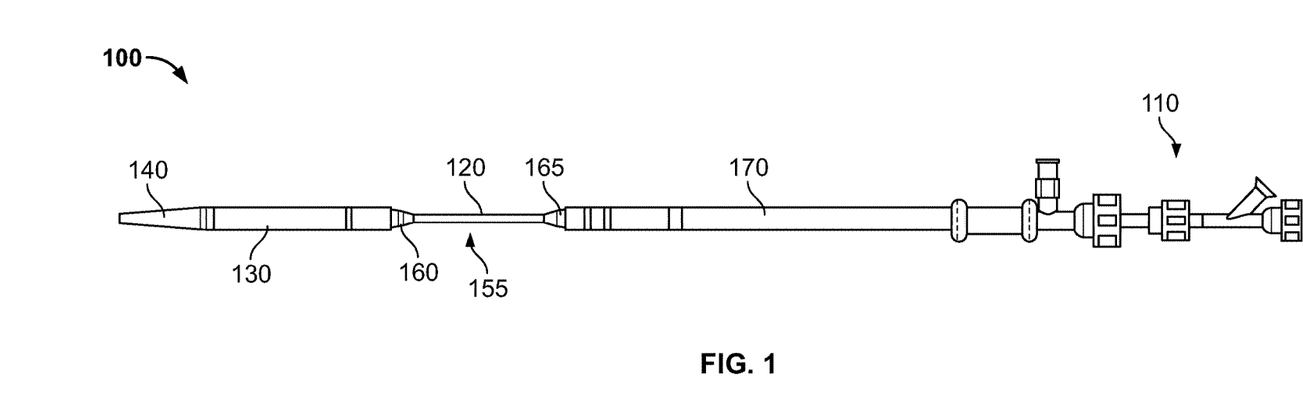
FIG. 1 is a side elevational view of a delivery system for a collapsible prosthetic heart valve, with a distal sheath in an open condition.
Figure 2:
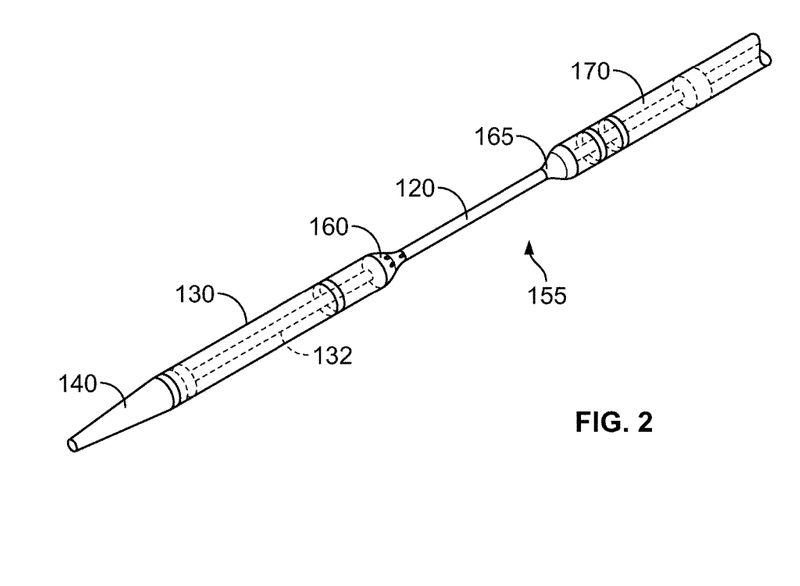
FIG. 2 is a perspective view of a distal portion of the delivery system of FIG. 1.
Figure 3:
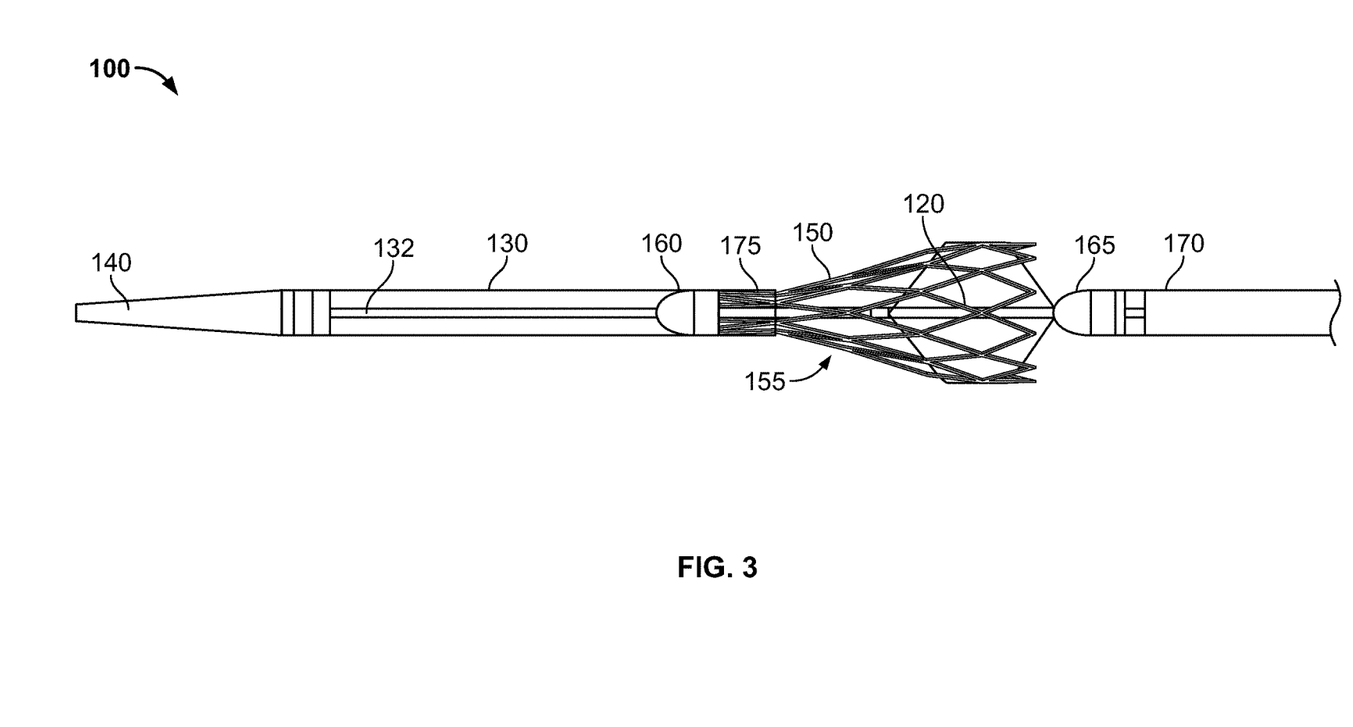
FIG. 3 is side elevational view of the distal portion of the transapical delivery device of FIG. 1 with a partially expanded collapsible prosthetic heart valve.

FIGS. 1-3 illustrate a delivery system 100 for transapically delivering any suitable collapsible prosthetic heart valve into a patient. Collapsible and re-expandable prosthetic heart valves are more fully described in U.S. Patent Application Publication No. 2011/0098800, the entire disclosure of which is hereby incorporated by reference herein. Delivery system 100 generally includes a manifold 110, a tubular shaft or valve support structure 120, a distal sheath 130, a proximal sheath 170, and an atraumatic tip 140.

Shaft 120 has a first retainer 165 fixedly connected to its proximal end and a second retainer 160 fixedly connected to its distal end so as to define a valve-receiving compartment 155 of a fixed dimension between the retainers. Compartment 155 is sized to receive a collapsible prosthetic heart valve 150 in an assembled condition. In that regard, retainer 160 may have a plurality of notches or pockets for receiving retention members (not shown) an prosthetic valve 150 so as to hold the aortic end of the heart valve in assembled relationship with delivery system 100. Transcatheter aortic valve delivery systems implementing retainers are more fully described in U.S. Patent Publication No. 2012/0078350, the entire disclosure of which is hereby incorporated by reference herein.

Proximal sheath 170 extends from a handle (not shown) to the fixed retainer 165. A conduit 132 extends through proximal sheath 170 to atraumatic tip 140, passing slidably through the lumen of shaft 120. At its proximal end, conduit 132 may be connected to the handle or may protrude therefrom for manipulation by the user of delivery system 100. The distal sheath 130 is connected to the atraumatic tip 140 so that sliding movement of conduit 132 results in a corresponding sliding movement of the distal sheath. That is, as conduit 132 is slid distally relative to shaft 120, distal sheath 130 is moved toward an open position uncovering the valve-receiving compartment 155 for deployment of the prosthetic heart valve 150, and as conduit 132 is slid proximally relative to shaft 120, the distal sheath is moved toward a closed position covering the valve-receiving compartment and maintaining the prosthetic heart valve in a collapsed condition. A proximal edge 175 of distal sheath 130 abuts retainer 165 when the distal sheath is in the closed position fully covering compartment 155. The proximal edge 175 of distal sheath 130 is spaced apart from retainer 165 when compartment 155 is at least partially uncovered, as shown in FIG. 3.

Conduit 132 is flexible enough to bend upon introduction or withdrawal from the body, as well as during articulation of the delivery system 100. However, conduit 132 retains enough stiffness to transmit force, such as when the conduit is slid distally, pushing the distal sheath 130 distally. Conduit 132 may have a lumen extending along its entire length for receiving a guide wire (not shown). The guide wire may extend through conduit 132 and out from delivery system 100 through a bore (not shown) extending longitudinally through atraumatic tip 140.

Figure 4A:
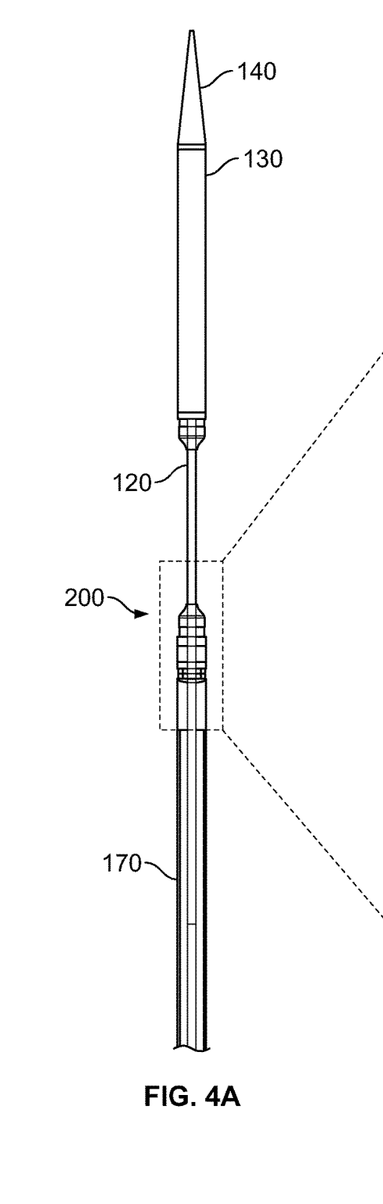
FIG. 4A is a side elevational view of the distal portion of the transapical delivery device of FIG. 1.

Referring to FIG. 4A, a transapical delivery system 100' is shown according to an embodiment of the invention. The delivery system 100' is generally similar to delivery system 100 described above, and further includes an articulation mechanism 200.

Figure 4B:
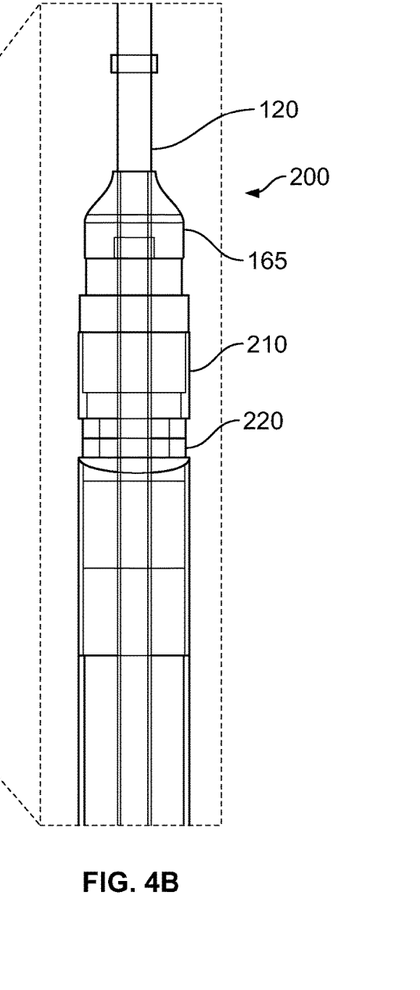
FIG. 4B is an enlarged detailed view of the articulation system of the delivery device of FIG. 4A.
Figure 5A:
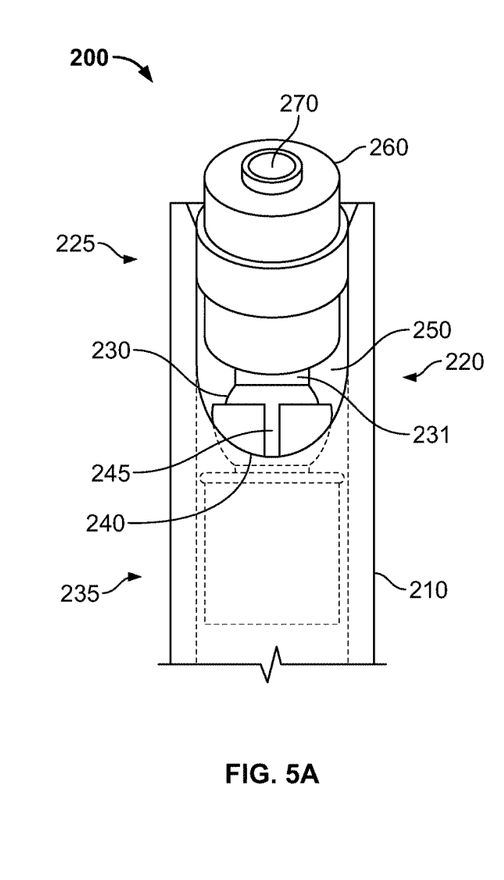
FIGS. 5A-5D are enlarged front and side views in partial cross-section of the articulation system shown in FIG. 4B.
Figure 5B:
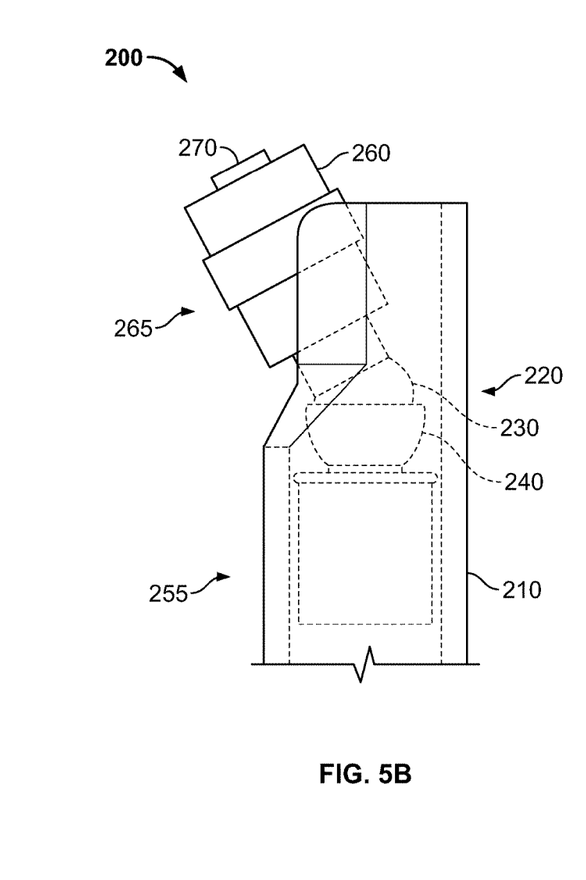
Figure 5C:
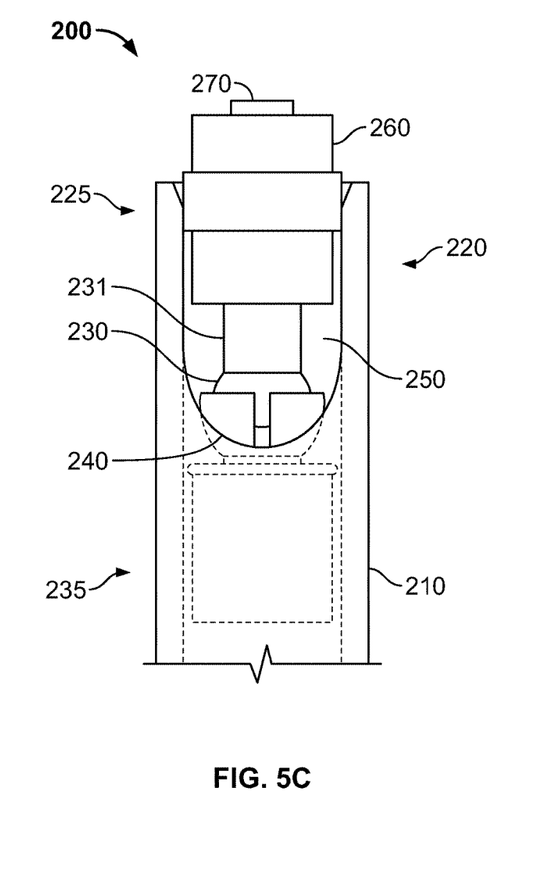
Figure 5D:
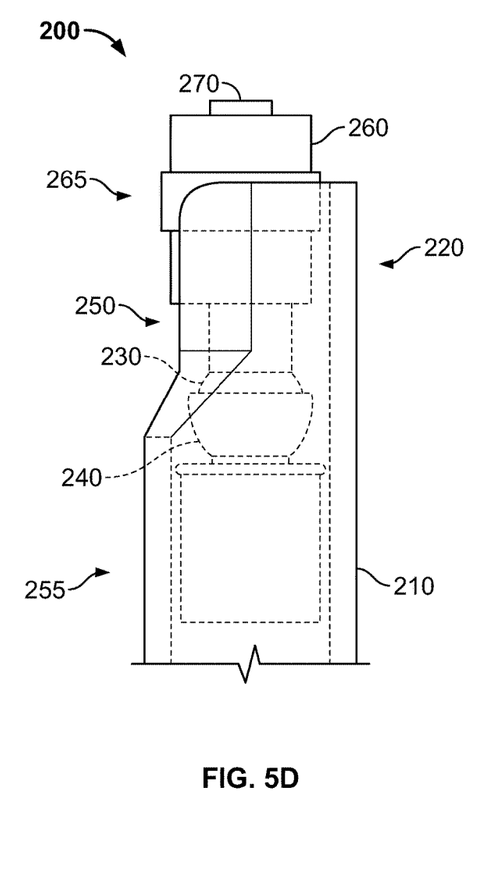

FIG. 4B shows a magnified view of articulation mechanism 200 with the body of delivery system 100' shown as partially transparent so that the components of the articulation mechanism can be more easily seen. The articulation mechanism 200 includes an articulating joint 220 disposed proximally of retainer 165. Referring to the detailed views in FIGS. 5A-D, the articulating joint 220 has a ball and socket configuration allowing 360 degrees of rotation. More particularly, joint 220 has a first portion 225 including a generally cylindrical body 260 with a hemispherical head or "ball" 230 on one end thereof. The ball 230 may be connected to the body 260 by a neck portion 231 which may be smaller in cross-section than the body. The other end of body 260 may be connected to retainer 165. A second or socket portion 235 of joint 220 may be press fit in the end of proximal sheath 170. A spherical end 240 of socket portion 235 has a shape that is complementary to ball 230 so as to define a surface against which the ball may pivot. Spherical end 240 may be sized and shaped to receive ball 230 in a snap fit or compression fit engagement to ensure that ball 230 is always in contact with the pivot surface.

Spherical end 240 may also include one or more slots 245 extending partially or fully through the diameter of the spherical end. The slots 245 may provide a level of expandability to the spherical end 240. This expandability may, for example, ease the insertion of ball 230 into spherical end 240 during assembly. The slots 245 may also provide spherical end 240 with a degree of compressibility, the purpose of which will become evident from the description below. The slots 245 may also serve other functions, the purpose of which will become evident from the description below. A bore 270 extending longitudinally through first portion 225 and socket portion 235 is sized to slidably receive conduit 132 therethrough.

A restrictive sheath 210 is slidably assembled over joint 220 so as to be movable between a lock position and a release position. Sheath 210 has a generally cylindrical structure with a U-shaped slot 250 formed in the cylindrical wall so as to extend longitudinally from the distal end thereof. The U-shaped slot 250 defines in sheath 210 a closed portion 255 (i.e., the portion without the U-shaped slot) and a partially open portion 265 (i.e., the portion with the U-shaped slot.) The width of slot 250 is larger than the widest, diameter of the body 260 of first portion 225, allowing the body to pass through the slot in the restrictive sheath 210 when the first portion pivots. When moved to the lock position, the closed portion 255 of sheath 210 covers at least a substantial portion of both first portion 225 and socket portion 235, thereby preventing ball 230 from pivoting against spherical end 240. In this lock position, the first portion 225 of the articulating joint 220 is prevented from pivoting relative to the socket portion 235, and the distal sheath 130 is locked in axial alignment with the longitudinal axis of the proximal sheath 170. In the release position, sheath 210 is moved away from the first portion 225 until the slot 250 exposes the entirety of body 260, thereby enabling the first portion to pivot relative to the socket portion 235. FIGS. 5A-5D show sheath 210 in the release position and the first portion 225 in different stages of articulation relative to the socket portion 235. When the first portion 225 is pivoted relative to the socket portion 235, the distal sheath 130 will be oriented at an angle transverse to the longitudinal axis of the proximal sheath 170. The first portion 225 is free to pivot in a single plane through the slot 250 of the restrictive sheath 210, preferably through an angle of about 0° to about 45° relative to the longitudinal axis of the proximal sheath 170. Benefits of the pivoting motion are explained more fully below in the description of the surgical use of the delivery system 100'.

In addition to being slidable relative to joint 220, the restrictive sheath 210 may also be rotatable about its longitudinal axis. A user can rotate the restrictive sheath 210 through an angle of 360° about its longitudinal axis, changing the position of slot 250 and, hence, the direction or plane in which the first portion 225 of joint 220 may pivot. This allows the user to control which plane the body 260 and, therefore, the distal sheath 130, may pivot in relation to the longitudinal axis of the proximal sheath 170. When in the look position, the restrictive sheath 210 is positioned within the distal sheath 130 (which is also in the closed position). This configuration allows the outer surface of the delivery system 100' to maintain a relatively flush surface near the point of contact between the restrictive sheath 210 and the distal sheath 130. As explained below, this configuration reduces the likelihood of blood leakage during insertion of the delivery system 100' through the apex of the heart. The proximal end of the restrictive sheath 210 may be operatively connected to a mechanism (not shown) outside the patient to enable the restrictive sheath to be retracted to the release position and advanced to the lock position. For example, the restrictive sheath 210 can extend proximally to a handle (not shown) of the delivery system 100' such that the user can manually pull or push the restrictive sheath as desired between the lock and release positions. In a preferred embodiment, the restrictive sheath 210 may be operatively connected to a wheel mechanism (not shown) near the handle of the delivery system 100' to provide the operator with fine control over the movement of the restrictive sheath between the lock and release positions. The restrictive sheath 210 may further include indicia that are visible using an imaging technique, such as fluoroscopy, to indicate the position of the restrictive sheath within the patient's heart. Alternatively, the delivery system 100' may include indicia that remain outside of the patient's body, but that are operatively connected to restrictive sheath 210 so as to provide an indication of its position within the heart.

When practicing an embodiment of the invention, a collapsible prosthetic heart valve 150 is collapsed around the shaft 120 of a delivery system 100' and held in place in compartment 155 by moving the distal sheath 130 to the closed position. The distal end of the delivery system 100' is advanced through an incision in the apex of the heart using conventional techniques well known in the art. The procedure may be performed on a beating heart using a purse string suture on the incision through which the delivery system 100' is advanced. The purse string suture allows the surgeon to insert the delivery system 100' into the heart through the incision, and tighten the incision around the delivery device by pulling the suture, allowing for a better seal between the heart, tissue and the delivery device. Because blood may be flowing through the heart during the procedure, it is preferable for the restrictive sheath 210 to be flush with the remainder of the body of the device to minimize any leakage when the articulation mechanism 200 passes into or out from the heart. Further, the restrictive sheath 210 preferably is in the lock position during insertion and withdrawal of the delivery system 100' to provide stability to the delivery system at the location of the articulation mechanism 200 and to ensure that articulation of the joint 220 does not occur prematurely.

Once the articulation mechanism 200 has passed into the heart, which may be indicated by visual, fluoroscopic or other markings on or connected to the restrictive sheath 210, the operator may choose to change the orientation of the distal sheath 130 to facilitate vale placement. To do so, the operator may retract the restrictive sheath 210 to the release position, allowing articulation of joint 220. Joint 220 may provide up to 360 degrees of articulation once the restrictive sheath 210 is in the release position. The articulation of joint 220 causes the distal end of the delivery system 100', including the distal sheath 130, to pivot with respect to the longitudinal axis of the proximal sheath 170. This pivoting provides the operator the ability to more precisely align the distal sheath 130 of the delivery system 100' with the native valve annulus, particularly when there is a significant mismatch between the apical and annular axes or interfering tissue structures, as described above. For example, if the apical and annular axes are not coaxial, it would be difficult or impossible to maintain the proximal end of an unbending delivery device coaxial with the entry point at the apex of the heart while simultaneously having the distal end of the delivery device containing the valve coaxial with the annulus in which the valve is to be deployed. The articulation joint 220 makes this possible, even when there is significant mismatch between the axis of the apex and the axis of the native valve annulus. Once the operator is satisfied that the distal sheath 130, and thus the prosthetic heart valve 150, is properly aligned with the native valve annulus, the heart valve may be deployed as described above and as is well known in the art. Prior to withdrawal of the delivery system 100' from the heart, the operator may advance the restrictive sheath 210 to the lock position to both, ensure a smooth outer surface of the device and provide stability at the articulation joint 220. Optionally, the proper location of the restrictive sheath 210 may be confirmed with visual indicia, such as visual or fluoroscopic markers, and then the delivery system 100' may be removed from the patient's heart.

Figure 6A:
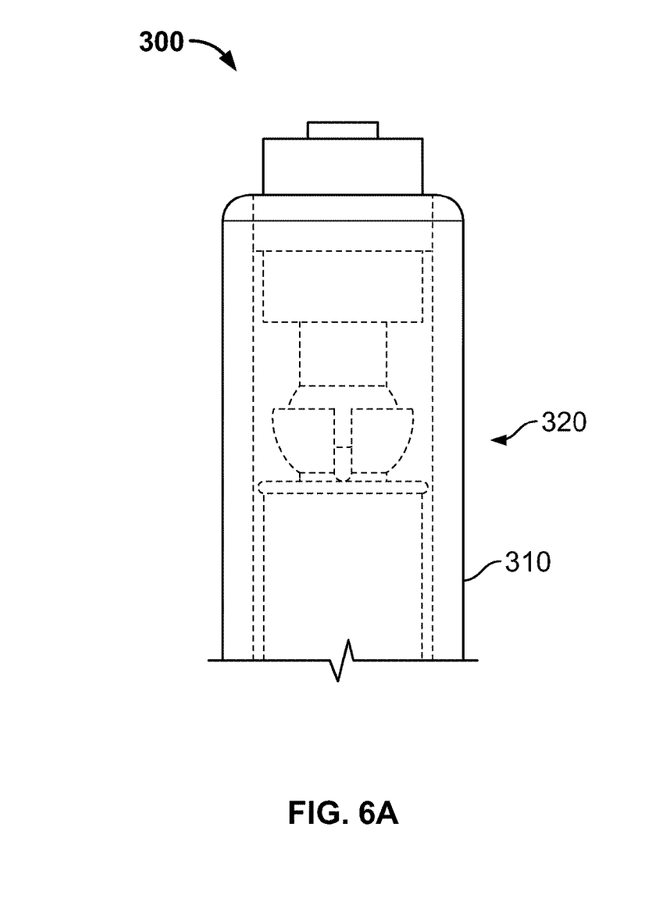
FIG. 6A is an enlarged front view of an alternate embodiment of an articulation system.
Figure 6B:
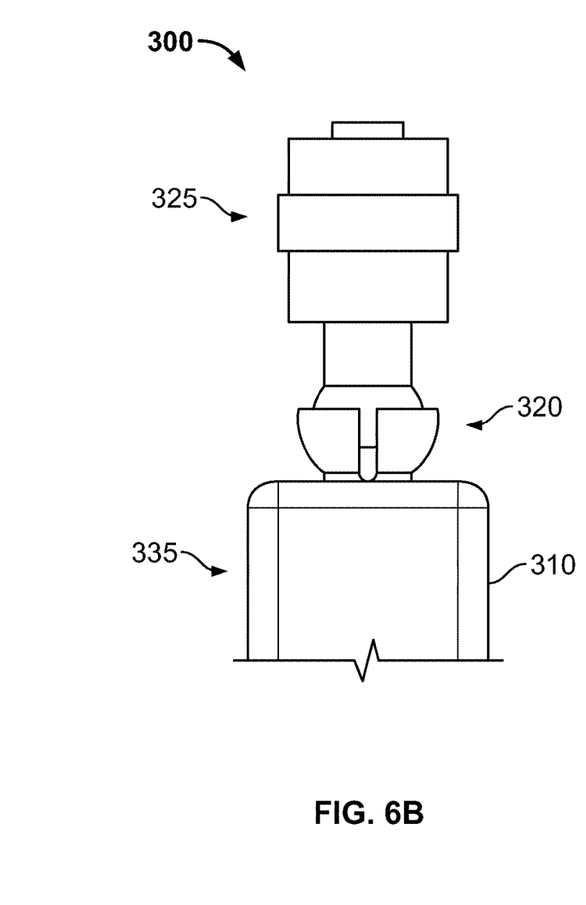
FIG. 6B is an enlarged front view of the articulation system of FIG. 6A, partially broken away to show elements thereof.

FIGS. 6A-B show an articulation mechanism 300 in accordance with an alternate embodiment. This embodiment is similar to articulation meschanism 200 described above, and includes an articulating joint 320 having a first portion 325 and a second or socket portion 335, and a restrictive sheath 310. In articulation mechanism 300, however, the restrictive sheath 310 does not have a U-shaped slot. When in the release position shown in FIG. 6B, the entirety of restrictive sheath 310 is proximal of the first portion 325, and therefore does not restrict the articulating joint 320 from pivoting in any plane to orient the distal sheath 130 at a transverse angle to the longitudinal axis of the proximal sheath 170. The first portion 325 may pivot through an angle of about 0° to about 45° relative to the longitudinal axis of the proximal sheath 170. When in the loch position shown in FIG. 6A, the restrictive sheath 310 covers at least a substantial portion of both the first portion 325 and the socket portion 335, thereby preventing these portions from pivoting relative to one another and locking the distal sheath 130 in axial alignment with the longitudinal axis of the proximal sheath 170.

Figure 7:
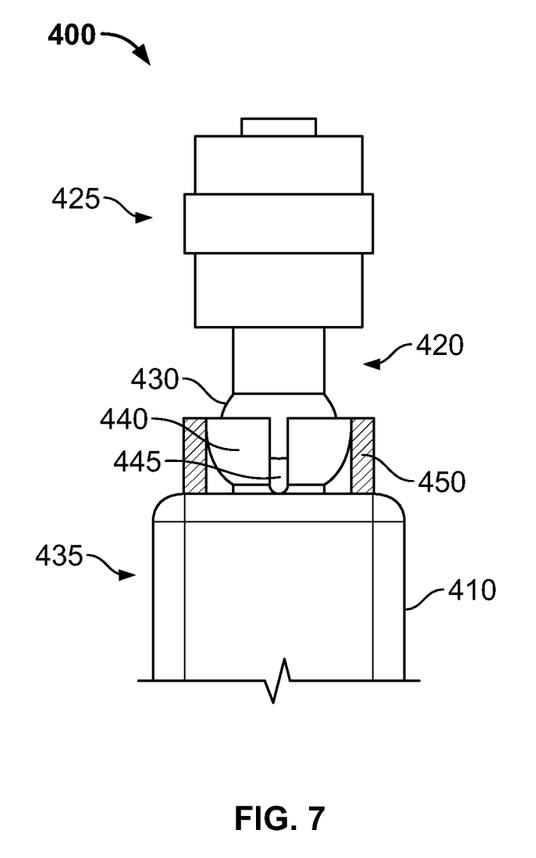
FIG. 7 is an enlarged front view of the articulation system of FIG. 6A, partially broken away to show the elements thereof, and with an articulation joint locking feature in a locked position.

An articulation mechanism 400 in accordance with yet a further embodiment is shown in FIG. 7. This embodiment is similar to articulation mechanisms 200 and 300 described above, and includes an articulating joint 420 having a first portion 425 and a second or socket portion 435, as well as a restrictive sheath 410. Articulation mechanism 400 further includes a chuck or locking sheath 450 for locking the articulating joint 420 at a selected angle. As described above, once inside the heart, the restrictive sheath 410 may be retracted to the release position to allow the joint 420, as well as the distal sheath 130 of the delivery system 100', to articulate. Once the distal sheath 130 is at a desired angle, for example an angle that aligns the distal sheath coaxially with the site of valve implantation, it may be desirable to lock the articulation joint 420 at the selected angle. If the joint 420 is not locked, movement of the delivery system 100' during the process of deploying the prosthetic valve may cause the distal sheath 130 to move relative to the proximal sheath 170 so that it is no longer in the desired orientation. A locking feature in the nature of locking sheath 450 can prevent or at least minimize such movements.

Locking sheath 450 may be in the form of a sheath extending from the proximal end of the delivery system 100' to the joint 420. At its proximal end, locking sheath 450 may be connected to a handle (not shown) or may protrude therefrom for manipulation by the user of the delivery system 100'. The locking sheath 450 may be positioned within the lumen of the restrictive sheath 410, and is moveable between a lock position and an unlock position. When the distal sheath 130 has been oriented at the desired angle, the locking sheath 450 may be advanced past the distal end of the restrictive sheath 410 and around the spherical end 440 of the socket portion 435 to the lock position (as shown in FIG. 7). The inner diameter of the locking sheath 450 may be smaller than the largest diameter of the spherical end 440 so that, in the lock position, the locking sheath 450 compresses the spherical end 440, which compression is enabled by the slots 445 provided in the spherical end. When the spherical end 440 of the socket portion 435 is compressed, there is an increase in friction between the spherical end 440 and ball 430, making it more difficult for the first portion 425 to pivot relative to the socket portion. When a user wishes to place the locking sheath into the unlock position, which may for example be desired after a prosthetic heart valve has been deployed from the delivery system, the user retracts the locking sheath 450 proximally. As the locking sheath 450 is retracted, the compression on the spherical end 440 is eliminated, which in turn reduces the friction between the spherical end and ball 430. Once the locking sheath 450 is in the unlock position, the user may advance the restrictive sheath 410 to the lock position to lock the distal sheath 130 in axial alignment with the longitudinal axis of the proximal sheath 170, enabling the delivery system to be withdrawn from the patient.

In an alternative embodiment, the locking feature can be a chuck similar to a drill chuck (not shown). In this embodiment, the chuck may partially or fully surround the spherical end 440 of socket portion 435 and may have a lock position and an unlock position. One or more pins or other protrusions may extend radially inward from the chuck. In the unlock position, the chuck may surround the spherical end 440 but provide little or no force thereon. To proceed to the lock position, the pins may be advanced radially inward toward the spherical end 440, for example, by rotating the chuck in a first direction. In the lock position, the pins may compress the spherical end 440 against the ball 430 with a radially inward force. When a user wishes to move the chuck to the unlock position, which may for example be desired after a prosthetic heart valve has been deployed from the delivery system, the user may retract the pins away from contact with the spherical end 440, which may for example be accomplished by rotating the chuck in a direction opposite the first direction. As the pins retract, the compression on the spherical end 440 is reduced, which in turn reduces the friction between the spherical end and ball 430. Once the chuck is in the unlock position, the user may advance the restrictive sheath 410 to the lock position to lock the distal sheath 130 in axial alignment with the longitudinal axis of the proximal sheath 170, enabling the delivery system to be withdrawn from the patient.

Although described with reference to the delivery of prosthetic heart valves, the delivery system described herein may be used to deliver any number of items into the human body. For example, stents, occluders, and other devices suitable for implantation in the body may be introduced using embodiments of the delivery system described herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present indention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A delivery system for delivering a medical device to an implantation site in a patient, comprising:
   a proximal sheath extending in a longitudinal direction;
   a distal sheath slidable relative to the proximal sheath;
   a compartment defined between a shaft and the distal sheath and adapted to receive the medical device in an assembled condition; and
   an articulating joint having a first portion directly coupled to the shaft and a second portion directly coupled to the proximal sheath, the first portion being pivotable relative to the second portion so as to pivot the compartment from a first orientation extending in the longitudinal direction to a second orientation extending transverse to the longitudinal direction,
   wherein a proximal end of the distal sheath is positioned distal of a distal end of the proximal sheath.

2. The delivery system according to claim 1, wherein the articulating joint comprises a ball and a socket.

3. The delivery system according to claim 2, further comprising a locking feature configured to compress the socket against the ball.

4. The delivery system according to claim 3, wherein the locking feature comprises a locking sheath slidable between a lock condition surrounding a largest cross-section of the socket and a release condition not surrounding the largest cross-section of the socket.

5. The delivery system according to claim 1, further comprising a restrictive sheath slidable relative to the articulating joint between a lock position and a release position.

6. The delivery system according to claim 5, wherein the restrictive sheath in the lock position at least partially circumscribes the articulating joint.

7. The delivery system according to claim 6, wherein the restrictive sheath in the release position at most partially circumscribes the articulating joint.

8. The delivery system according to claim 7, wherein the restrictive sheath includes a slot having a width greater than a width of the first portion of the articulating joint, such that the first portion of the articulating joint can pivot through the slot in a single plane when the restrictive sheath is in the release position.

9. The delivery system according to claim 8, wherein the restrictive sheath is rotatable about an axis extending in the longitudinal direction, whereby rotation of the restrictive sheath changes the plane in which the first portion of the articulating joint can pivot.

10. The delivery system of claim 5, wherein the restrictive sheath includes a proximal portion and a distal portion, the distal portion of the restrictive sheath being proximal to the first portion of the articulating joint when the restrictive sheath is in the release position.

11. The delivery system of claim 10, wherein the first portion of the articulating joint is configured to pivot in any plane relative to the second portion of the articulating joint when the restrictive sheath is in the release position.

12. The delivery system according to claim 5, wherein the restrictive sheath is rotatable about an axis extending in the longitudinal direction.

13. The delivery system according to claim 5, wherein the restrictive sheath is operatively connected to a retraction mechanism at a proximal end of the delivery system.

14. The delivery system according to claim 5, wherein the restrictive sheath includes visual indicia of location.

15. The delivery system according to claim 14, wherein the visual indicia comprise line markings.

16. The delivery system according to claim 14, wherein the visual indicia comprise fluoroscopic markings.

17. A delivery system for delivering a medical device, comprising:
   a proximal sheath extending in a longitudinal direction;
   a distal sheath slidable relative to the proximal sheath;
   a compartment defined between a shaft and the distal sheath when the distal sheath at least partially surrounds the shaft;
   a collapsible prosthetic heart valve mounted in the compartment in a collapsed condition;
   an articulating joint having a first portion directly coupled to the shaft and a second portion directly coupled to the proximal sheath, the first portion being pivotable relative to the second portion so as to pivot the compartment from a first orientation extending in the longitudinal direction to a second orientation extending transverse to the longitudinal direction; and
   a restrictive sheath slidable relative to the articulating joint between a lock position and a release position, the restrictive sheath at least partially circumscribing the articulating joint in the lock position and at most partially circumscribing the articulating joint in the release position, wherein a proximal end of the distal sheath is positioned distal of a distal end of the proximal sheath.

* * * * *